United States Patent
Larem et al.

(10) Patent No.: US 10,000,718 B2
(45) Date of Patent: Jun. 19, 2018

(54) SULPHUR-BRIDGED COMPOUNDS, USE THEREOF AND PROCESS FOR PRODUCTION THEREOF

(71) Applicant: Rhein Chemie Rheinau GmbH, Mannheim (DE)

(72) Inventors: David Larem, Eppertshausen (DE); Sandra Horstmann, Mannheim (DE); Thomas Rossrucker, Oestringen (DE); Markus Kuilder, Oftersheim (DE); Michael Koenig, Mannheim (DE)

(73) Assignee: LANXESS Deutschland GmbH, Cologne (DE)

( * ) Notice: Subject to any disclaimer, the term of this patent is extended or adjusted under 35 U.S.C. 154(b) by 135 days.

(21) Appl. No.: 14/254,026

(22) Filed: Apr. 16, 2014

(65) Prior Publication Data

US 2014/0323373 A1 Oct. 30, 2014
US 2016/0264903 A2 Sep. 15, 2016

(30) Foreign Application Priority Data

Apr. 24, 2013 (EP) .................................... 13165029

(51) Int. Cl.
| | | |
|---|---|---|
| *C07C 69/34* | (2006.01) | |
| *C10L 1/19* | (2006.01) | |
| *C08G 64/00* | (2006.01) | |
| *C10M 135/06* | (2006.01) | |
| *C07C 323/52* | (2006.01) | |
| *C10M 135/26* | (2006.01) | |

(52) U.S. Cl.
CPC .......... *C10M 135/06* (2013.01); *C07C 323/52* (2013.01); *C10M 135/26* (2013.01); *C10M 2219/024* (2013.01); *C10M 2219/085* (2013.01); *C10N 2270/00* (2013.01)

(58) Field of Classification Search
CPC . C10M 151/00; C10M 135/02; C10M 135/06
USPC ........................................ 508/465, 494, 492
See application file for complete search history.

(56) References Cited

U.S. PATENT DOCUMENTS 3,822,299 A * 7/1974 Lukeman ............... C08G 65/22
508/223
4,172,800 A 10/1979 Walker

OTHER PUBLICATIONS

"Washing and Cleansing Agents Act", Section 9, Sulfur Carriers, 2003, pp. 259, 260, 277-281.
Chemistry and Technology of Surfactants, Non-ionic Surfactants, 2006, pp. 139-140.
Lubricants and Lubrication, 2001, p. 107.

* cited by examiner

*Primary Examiner* — James C Goloboy
*Assistant Examiner* — Francis C Campanell

(57) ABSTRACT

The present invention relates to novel sulphur-bridged compounds, in which within the molecule there is at least one fatty acid bonded by way of at least one sulphur bridge to at least one polyalkylene glycol ester, the reaction product of a fatty acid with a polyalkylene glycol, and these have from 8 to 29% by weight sulphur content, to use of these as sulphur carrier and lubricant additive and to production of the said compounds.

16 Claims, No Drawings

SULPHUR-BRIDGED COMPOUNDS, USE THEREOF AND PROCESS FOR PRODUCTION THEREOF

The present invention relates to novel sulphur-bridged compounds, in which within the molecule there is at least one fatty acid bonded by way of at least one sulphur bridge to at least one polyalkylene glycol ester, the reaction product of a fatty acid with a polyalkylene glycol, and these have from 8 to 29% by weight sulphur content, to use of these as sulphur carrier and lubricant additive and to production of the said compounds.

In Lubricant Additives, 2003, pp. 259 and 260 it is said that sulphur carriers are of a class of organic compounds in which the oxidation state of the sulphur is 0 or −1 and the sulphur atom is bonded either to a hydrocarbon or to a sulphur atom. It is moreover explained that sulphur carriers have no other heteroatoms except for oxygen. The sulphur carriers are produced by adding sulphur to any of the types of unsaturated compounds which comprise double bonds.

Sulphur carriers are mainly used as additive in lubricants. According to the customary classification of lubricant additives, sulphur carriers are classified with the high-pressure additives (=EP Additive) group, on the basis of their superior effectiveness. Sulphur carriers primarily prevent the fusion of two metallic materials in frictional contact with one another, and specifically under high loading and at high temperature. In Lubricants and Lubrication, 2001, p. 107, it is said that the sulphur present reacts with the metal surface, the temperatures at which this reaction takes place generally being above 600° C. The low-friction layers resulting from the reaction are continuously sheared away by a type of controlled wear process, and this prevents fusion of the metal surfaces.

Sulphur carriers also reduce friction between two metallic materials in frictional contact with one another, this effect being mainly important under low loading and at low temperature. The lubricant power of the sulphur carrier is a decisive factor in friction reduction. In Lubricant Additives, 2003, p. 277 it is said that the lubricant power of sulphur carriers generally rises with increasing polarity.

Sulphur carriers composed of sulphur-bridged triglycerides and/or fatty acid alkyl esters are produced from unsaturated triglycerides and/or unsaturated fatty acid alkyl esters which are then sulphur-bridged. Sulphur-bridged triglycerides and/or fatty acid alkyl esters have the disadvantage of being immiscible with water. When they are used in water-miscible lubricants it is therefore necessary to add emulsifiers.

Sulphur carriers composed of sulphur-bridged fatty acids are produced from unsaturated fatty acids which are sulphur-bridged. The sulphur-bridged fatty acids are primarily used as additive for water-miscible lubricants. In the production of water-miscible lubricants, the sulphur-bridged fatty acids are normally neutralized to give soaps, because the standard procedure adds bases, for example triethanolamine or aqueous potassium hydroxide solution, in order to establish an alkaline pH. The resultant sulphur-bridged soaps are water-miscible and require no addition of emulsifier, but instead can themselves act as emulsifier. They are moreover strongly polar and have high lubricant power on metallic materials.

However, sulphur-bridged soaps have the disadvantage that in hard water they can produce soap scum deposit, as by way of example described in Lubricant Additives, 2003, p. 281. Various approaches to a solution, for example adapting the lubricant formulation to be appropriate to a prescribed water-hardness range or the use of complexing agents, have hitherto been found to provide only a partial solution. Satisfactory use of sulphur-bridged fatty acids as additive for water-miscible lubricants is generally possible only at high cost. This greatly restricts their use.

In U.S. Pat. No. 4,172,800 and U.S. Pat. No. 3,822,299, unsaturated fatty acids are first ethoxylated and then reacted with sulphur to give sulphur-bridged fatty acid polyalkylene glycol esters. The products described have no carboxylic acid unit. These products cannot be used cost-effectively, because of low sulphur content of less than 8% by weight, and/or are not fully water-miscible. In Example 2 of U.S. Pat. No. 3,822,299, a comparatively high sulphur content of 10.9% by weight is achieved. Calculation of the HLB value according to W. C. Griffin gives an HLB value of 7.5. Accordingly, when the product from Example 2 has been diluted in water it forms a semi-stable emulsion, and it is therefore not fully water-miscible.

All of the sulphur carriers known hitherto require addition of emulsifiers for full miscibility in water and/or have low polarity and/or tend to form soap scum deposit in hard water and/or have low sulphur content. For the purposes of the invention, hard water means a hardness level, expressed in German degrees, of at least 8.4° dH. This corresponds to the "moderate" and "hard" hardness ranges according to the German "Wasch- und Reinigungsmittelgesetz [Washing and Cleansing Agents Act]", 2007.

The object of the present invention therefore consisted in providing sulphur-bridged compounds which are fully water-miscible without addition of emulsifiers and moreover have strong polarity, have no, or no significant, tendency toward formation of soap scum deposit in hard water and have sulphur content of at least 8% by weight.

Surprisingly, it has now been found that this object is achieved via sulphur-bridged compounds in which within the molecule there is at least one fatty acid bonded by way of at least one sulphur bridge to at least one polyalkylene glycol ester, the reaction product of a fatty acid with a polyalkylene glycol, and by virtue of the sulphur bridge(s) these compounds have from 8 to 29% by weight sulphur content.

The present invention provides sulphur-bridged compounds in which within the molecule there is at least one fatty acid bonded by way of at least one sulphur bridge to at least one polyalkylene glycol ester, the reaction product of a fatty acid with a polyalkylene glycol, and by virtue of the sulphur bridge(s) these compounds have from 8 to 29% by weight sulphur content.

The polyalkylene glycol ester is preferably polyethylene glycol ester, polypropylene glycol ester, polybutylene glycol ester and/or polyalkylene glycol esters in which the ethylene oxide units, propylene oxide units and/or butylene oxide units are in random and/or blockwise arrangement. Particular preference is given to polyethylene glycol ester. In the text hereinafter, another term used for the polyalkylene glycol esters is polyalkylene-glycol-esterified fatty acids.

The sulphur-bridged compounds of the invention, based on monofunctional polyethylene glycol and on monounsaturated monocarboxylic acids can be represented diagrammatically by the following formula (I):

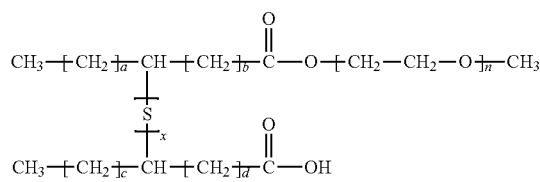

(I)

The sulphur-bridged compounds of the invention, based on bifunctional polyethylene glycol and on monounsaturated monocarboxylic acids can be represented diagrammatically by the following formula (II):

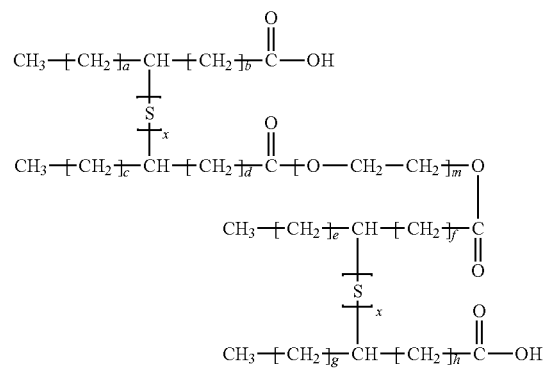

(II)

The sulphur-bridged compounds of the invention, based on trifunctional polyethylene glycol and on monounsaturated monocarboxylic acids can be represented diagrammatically by the following formula (III):

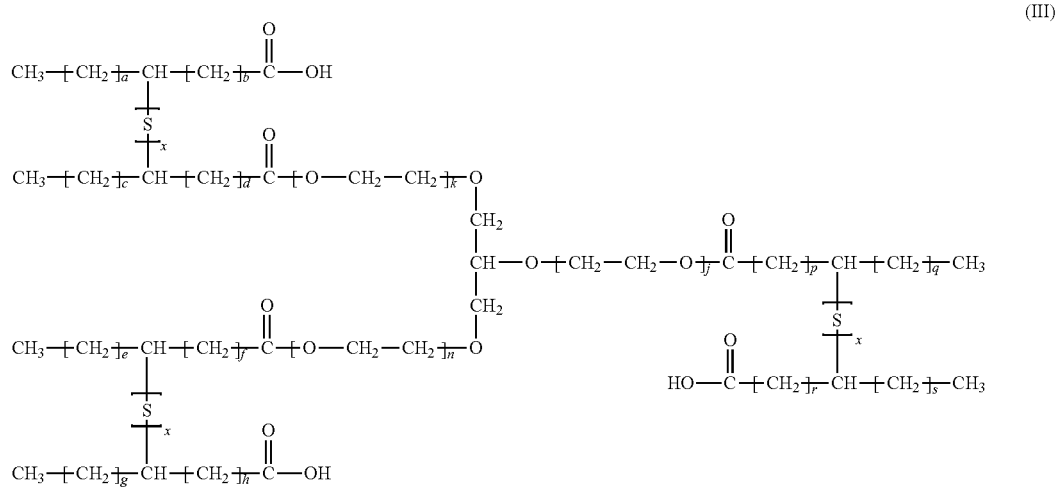

(III)

The sulphur-bridged compounds of the invention, based on tetrafunctional polyethylene glycol and on monounsaturated monocarboxylic acids can be represented diagrammatically by the following formula (IV):

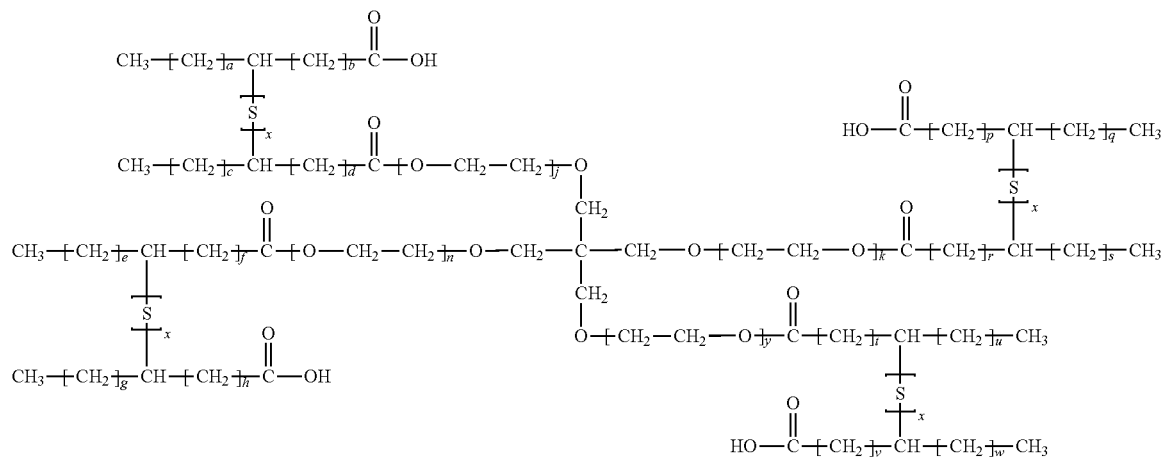

(IV)

For the indices stated, preference is given to the numerical ranges below:

| Index | Numerical range | Preferred numerical range |
|---|---|---|
| a | from 3 to 29 | from 5 to 12 |
| b | from 3 to 29 | from 5 to 12 |
| c | from 3 to 29 | from 5 to 12 |
| d | from 3 to 29 | from 5 to 12 |
| e | from 3 to 29 | from 5 to 12 |
| f | from 3 to 29 | from 5 to 12 |
| g | from 3 to 29 | from 5 to 12 |
| h | from 3 to 29 | from 5 to 12 |
| p | from 3 to 29 | from 5 to 12 |
| q | from 3 to 29 | from 5 to 12 |
| r | from 3 to 29 | from 5 to 12 |
| s | from 3 to 29 | from 5 to 12 |
| t | from 3 to 29 | from 5 to 12 |
| u | from 3 to 29 | from 5 to 12 |
| v | from 3 to 29 | from 5 to 12 |
| w | from 3 to 29 | from 5 to 12 |
| n | from 2 to 10 | from 4 to 8 |
| m | from 4 to 20 | from 8 to 16 |
| k | from 2 to 10 | from 4 to 8 |
| j | from 2 to 10 | from 4 to 8 |
| x | from 1 to 10 | from 2 to 4 |
| y | from 2 to 10 | from 4 to 8 |

The formulae II, III and IV can also comprise further units, for example polyethylene glycol esters, sulphur bridges and/or saturated monocarboxylic acids. The sulphur-bridged compounds represented in all of the formulae are based on polyethylene glycols. The invention also encompasses, alongside the polyethylene glycols, polypropylene glycols, polybutylene glycols and/or polyalkylene glycols in which the ethylene oxide units, propylene oxide units and/or butylene oxide units are in random and/or blockwise arrangement. It is moreover possible to use the monofunctional, bifunctional, trifunctional and tetrafunctional polyalkylene glycols in the form of mixture. It is also possible to use, alongside the monounsaturated monocarboxylic acids, unsaturated fatty acids which have any desired number of double bonds, triple bonds and/or carboxylic acid units.

The sulphur-bridged compounds of the invention can be produced by way of the 3 embodiments specified below, preference being given here to the first embodiment:

1) The sulphur-bridged compounds obtainable via the reaction of the unsaturated fatty acids with sulphur and/or hydrogen sulphide to give sulphur-bridged fatty acids, preferably sulphur-bridged saturated fatty acids, and the subsequent reaction of these sulphur-bridged fatty acids with polyalkylene glycol.
2) The sulphur-bridged compounds are obtainable via the reaction of the unsaturated fatty acids with polyalkylene glycol to give the intermediate product composed of unsaturated polyalkylene glycol ester and unesterified unsaturated fatty acid, and the subsequent reaction of this intermediate product with sulphur and/or hydrogen sulphide.
3) The sulphur-bridged compounds are obtainable via mixing of the unsaturated fatty acids with unsaturated fatty acid polyalkylene glycol esters which result from a reaction of unsaturated fatty acids with polyalkylene glycol or with alkylene oxides, and the subsequent reaction of this mixture with sulphur and/or hydrogen sulphide.

For the purposes of this invention, polyalkylene glycol is a monofunctional, bifunctional, trifunctional and/or tetrafunctional polyalkylene glycol.

The monofunctional polyalkylene glycols are preferably linear polyalkylene glycols which have one hydroxy group, where alkylene is preferably ethylene, propylene and/or butylene, particularly preferably ethylene. The molar mass of the monofunctional polyalkylene glycols is preferably from 100 to 500 g/mol. These can be produced via the reaction of monofunctional alcohols, preferably methanol, with alkylene oxides. The monofunctional polyalkylene glycols are by way of example obtainable with trade name Polyglykol M from Clariant International AG.

The bifunctional polyalkylene glycols are preferably linear polyalkylene glycols which have two hydroxy groups, where alkylene is preferably ethylene, propylene and/or butylene, particularly preferably ethylene. The molar mass of the bifunctional polyalkylene glycols is preferably from 200 to 1000 g/mol. These can be produced via the reaction of bifunctional alcohols, preferably ethylene glycol or diethylene glycol, with alkylene oxides. The bifunctional polyalkylene glycols are by way of example obtainable with trade name Pluriol® E from BASF SE.

The trifunctional polyalkylene glycols are preferably branched polyalkylene glycols which have three hydroxy groups, where alkylene is preferably ethylene, propylene and/or butylene, particularly preferably ethylene. The molar mass of the trifunctional polyalkylene glycols is preferably from 300 to 1500 g/mol. These can be produced via the reaction of trifunctional alcohols, preferably glycerol, with alkylene oxides. The trifunctional polyalkylene glycols are by way of example obtainable with trade name Ucon™ TPEG from The Dow Chemical Company.

The tetrafunctional polyalkylene glycols are preferably branched polyalkylene glycols which have four hydroxy groups, where alkylene is preferably ethylene, propylene and/or butylene, particularly preferably ethylene. The molar mass of the tetrafunctional polyalkylene glycols is preferably from 400 to 2000 g/mol. These can be produced via the reaction of tetrafunctional alcohols, preferably pentaerythritol, with alkylene oxides. The tetrafunctional polyalkylene glycols are by way of example obtainable with trade name Polyglykol P41 from Clariant International AG.

Among the abovementioned alkylene oxides, preference is given to ethylene oxide, propylene oxide and/or butylene oxide. These are obtainable commercially by way of example from BASF SE.

The production of polyalkylene glycols is described in general terms in Lubricants and Lubrication, 2001, p. 75.

The at least one fatty acid and the at least one polyalkylene-glycol-esterified fatty acid (polyalkylene glycol ester) preferably involves unsaturated carboxylic acids, preferably unsaturated monocarboxylic acids, which preferably have a carbon-chain length of from 6 to 32 C atoms. Starting materials that can be used are not only pure unsaturated monocarboxylic acids but also mixtures of monocarboxylic acids which comprise unsaturated monocarboxylic acids as main constituents and saturated monocarboxylic acids as ancillary constituents.

The reaction with sulphur and, respectively, polyalkylene glycol uses unsaturated fatty acids, preferably unsaturated monocarboxylic acids. Preference is given here to oleic acid and linoleic acid, which are used as main constituents of a fatty acid mixture in one particularly preferred embodiment of the invention.

The fatty acid mixtures are preferably obtained from oils of natural origin, and can also comprise a proportion of saturated fatty acids alongside the unsaturated fatty acids. Examples of oils of natural origin are babassu oil, cottonseed oil, borage oil, safflower oil, peanut oil, blackcurrant seed oil, hazelnut oil, herring oil, tung oil, jojoba oil, coconut oil, neatsfoot oil, bone oil, lard oil (=pork lard), liver oil, linseed oil, corn oil, almond oil, olive oil, palm oil, palm kernel oil, rapeseed oil, beef tallow oil (=beef lard), castor oil, sardine oil, mustard seed oil, soya bean oil, sunflower oil, shea butter, tall oil, grapeseed oil, whale oil and walnut oil. Refined variants of these are preferably used. Preference is given here to fatty acid mixtures which include more than 80% by weight of unsaturated fatty acids.

The unsaturated fatty acid polyalkylene glycol esters which are used as starting material according to the third embodiment are produced via the reaction of unsaturated fatty acids with polyalkylene glycols or alkylene oxides. These are products which are obtainable commercially but which however, as mentioned above, can also be produced via the reaction of unsaturated fatty acids with polyalkylene glycols or alkylene oxides. In this connection, in relation to the preferred unsaturated fatty acids, polyalkylene glycols and alkylene oxides reference is made to what has been said above. This reaction of unsaturated fatty acids with polyalkylene glycols is preferably carried out at temperatures of from 120 to 200° C. and at pressures of from 20 mbar to atmospheric pressure and with a reaction time of from 4 to 24 h with use of an acidic catalyst. The reaction of unsaturated fatty acids with alkylene oxides is preferably carried out at a temperature of from 100 to 190° C. and at a pressure of from 1 to 6 bar with use of a nucleophilic catalyst. The unsaturated fatty acid polyalkylene glycol esters are obtainable by way of example from Sasol Germany GmbH with trademarks Marlosol® and Marlowet®.

The production of fatty acid polyalkylene glycol esters is described in general terms in Chemistry and Technology of Surfactants, 2006, pp. 139 and 140.

The sulphur-bridged compounds of the invention can also be a constituent of a mixture.

The invention further provides mixtures comprising the sulphur-bridged compounds of the invention and additionally further additives and/or carrier liquids.

Preference is given here to further high-pressure additives, sulphur additives, antiwear additives, phosphorus additives, corrosion inhibitors, sulphonates, sulphonic acids, sulphonic esters, carboxylates, carboxylic acids, carboxylic esters, nonferrous-metal deactivators, triazoles, triazole derivatives, surfactants, emulsifiers, dispersing agents, solubilizers, carboxylic acid alkoxylates, carboxamides, fatty alcohols, fatty alcohol alkoxylates, ether carboxylic acids, glycols, glycol ethers, polyalkylene glycols, alkalizers, alkylamines, alkanolamines, lubricity improvers, monoglycerides, diglycerides, triglycerides, biocides, antifoams, antioxidants, complexing agents, sequestering agents, demulsifiers, viscosity-index improvers, flame retardants, dyes, odorants, and also Group I to V oils according to the definition of the American Petroleum Institute (API).

The present invention further provides processes for the production of the sulphur-bridged compounds of the invention:

Preference is given here to the 3 embodiments specified below.

1) The unsaturated fatty acid, preferably the unsaturated monocarboxylic acid, is first reacted with sulphur and/or hydrogen sulphide to give the sulphur-bridged fatty acid, preferably sulphur-bridged saturated fatty acid, and then this sulphur-bridged fatty acid is reacted with at least one polyalkylene glycol in such a way that at least one carboxylic acid unit of the fatty acid is present within the sulphur-bridged compounds of the invention.

2) A molar excess of unsaturated fatty acid, preferably of unsaturated monocarboxylic acid, is reacted with at least one polyalkylene glycol to give the intermediate product composed of unsaturated polyalkylene glycol ester and unesterified unsaturated fatty acid, and then this intermediate product is reacted with sulphur and/or hydrogen sulphide in such way that at least one carboxylic acid unit of the fatty acid is present within the sulphur-bridged compounds of the invention.

3) The unsaturated fatty acid, preferably the unsaturated monocarboxylic acid, is mixed with at least one unsaturated fatty acid polyalkylene glycol ester and then this mixture is reacted with sulphur and/or hydrogen sulphide in such a way that at least one carboxylic acid unit of the fatty acid is present within the sulphur-bridged compounds of the invention.

The determination of the carboxylic acid unit takes place by way of the acid number according to ASTM D664 or DIN 53402. In the first and second embodiments of the process of the invention, the reaction of the fatty acid and/or sulphur-bridged fatty acid with the polyalkylene glycol is detected via the acid-number. The juncture at which the reaction is terminated is no later than that at which at least one carboxylic acid unit is still present.

The first and second embodiment of the process of the invention preferably use the starting materials in the following ratios:
a) Based on 1 g of unsaturated fatty acid, preferably unsaturated monocarboxylic acid, from 0.05 g to 1 g of polyalkylene glycol is used;
and
b) based on 1 g of unsaturated fatty acid, preferably unsaturated monocarboxylic acid, from 0.05 g to 0.5 g of sulphur is used.

The third embodiment of the process of the invention preferably uses the starting materials in the following ratios:
a) Based on 1 g of unsaturated fatty acid, preferably unsaturated monocarboxylic acid, from 0.2 g to 4 g of unsaturated fatty acid polyalkylene glycol ester is used;
and
b) based on 1 g of unsaturated fatty acid, preferably unsaturated monocarboxylic acid, from 0.05 g to 0.5 g of sulphur is used.

In all of the embodiments of the processes of the invention, the reaction with sulphur and/or hydrogen sulphide ("sulphurization") is preferably carried out at pressures from atmospheric pressure (i.e. in the range from 0.9 to 1.1 bar) to 15 bar and at temperatures of from 119 to 170° C. and with a reaction time of from 4 to 24 h.

In the first and second embodiment of the process of the invention, it is preferable that the esterification is carried out at atmospheric pressure (i.e. in the range from 0.9 to 1.1 bar), with subsequent reduction to pressures extending as far as 10 mbar, the reaction being carried out at temperatures of from 120 to 200° C. and with a reaction time of from 4 to 24 h.

In the third embodiment of the process of the invention, the mixing is preferably carried out at atmospheric pressure and at temperatures of from 15 to 100° C. and with a mixing time of from 5 to 30 min.

In further embodiments of the present invention, preference is given to the reaction conditions specified below:

In the first embodiment of the process of the invention, it is preferable that the unsaturated fatty acid, preferably the unsaturated monocarboxylic acid, is first reacted with sulphur and/or hydrogen sulphide and then with polyalkylene glycol, preferably polyethylene glycol, to give the sulphur-bridged compounds of the invention. In the first step, the unsaturated monocarboxylic acid is sulphurized with sulphur and/or hydrogen sulphide in a pressure reactor at from atmospheric pressure to 15 bar, preferably 4 bar, and at from 119 to 170° C., preferably 130° C. The sulphurization is preferably catalysed by amines, metal oxides or acids. In the second step, the intermediate product is esterified with polyalkylene glycol, preferably polyethylene glycol at from atmospheric pressure to 10 mbar and at from 120 to 200° C., preferably 180° C. The esterification is preferably continued until no further water is removed by distillation. The esterification is preferably catalysed by tin salts or by acids, preferably by phosphoric acid and/or p-toluenesulphonic acid.

In the second embodiment of the process of the invention, it is preferable that a molar excess of unsaturated fatty acid, preferably the unsaturated monocarboxylic acid, is first reacted with polyalkylene glycol, preferably polyethylene glycol, and then with sulphur and/or hydrogen sulphide to give the sulphur-bridged compounds of the invention. In the first step, the unsaturated monocarboxylic acid is esterified with polyalkylene glycol, preferably polyethylene glycol, at from atmospheric pressure to 10 mbar and at from 120 to 200° C., preferably 180*C. The esterification is preferably continued until no further water is removed by distillation. The esterification is preferably catalysed by tin salts or by acids, preferably by phosphoric acid or p-toluenesulphonic acid. In the second step, the intermediate product which comprises unsaturated polyalkylene glycol ester and unesterified unsaturated fatty acid is sulphurized with sulphur and/or hydrogen sulphide in a pressure reactor at from atmospheric pressure to 15 bar, preferably 4 bar, and at from 119 to 170° C., preferably 130° C. The sulphurization is preferably catalysed by amines, metal oxides or acids.

In the third embodiment of the process of the invention, the unsaturated fatty acid, preferably the unsaturated monocarboxylic acid, is first mixed with the unsaturated fatty acid polyalkylene glycol ester and then reacted with sulphur and/or hydrogen sulphide to give the sulphur-bridged compounds of the invention. In the first step, the unsaturated monocarboxylic acid is mixed with the unsaturated fatty acid polyalkylene glycol esters at atmospheric pressure and from 15 to 100° C., preferably 40° C. In the second step, the mixture is sulphurized with sulphur and/or hydrogen sulphide in a pressure reactor at from atmospheric pressure to 15 bar, preferably 4 bar, and at from 120 to 170° C., preferably 130° C. The sulphurization is preferably catalysed by amines, metal oxides or acids.

The present invention further provides a process for the production of a mixture according to which lubricant additives and carrier liquids are additionally added before, during or after the production of the sulphur-bridged compounds of the invention.

The addition process can use commercially available mixing assemblies, preferably stirred tanks.

The present invention further provides the use of the sulphur-bridged compounds of the invention as sulphur carrier and/or as lubricant additive in all lubricants according to ISO 6743, for example preferably lubricants for metalworking or lubricants for machinery.

The sulphur-bridged compounds of the invention are preferably used as lubricant additive in water-miscible or water-mixed cutting fluids. These are described in DIN 51385.

The scope of the invention encompasses combinations of all of the moiety definitions, indices, parameters and explanations provided above and listed below in general terms or in preferred ranges, i.e. also encompasses any desired combination between the respective ranges and preferred ranges.

The examples below serve to illustrate the invention without any resultant limiting effect.

INVENTIVE EXAMPLES

In the Example that follows, the percentages relate to % by weight.
Reagents:
Additin® RC 5250, sulphur-bridged fatty acids based on a vegetable fatty acid mixture (composed of: >90% by weight of unsaturated fatty acids, main constituents oleic acid and linoleic acid), with sulphur content about 15% by weight; producer: Rhein Chemie Rheinau GmbH.

Pluriol® E 600, linear bifunctional polyethylene glycol, average molar mass: about 600 g/mol; producer: BASF SE.

The following components were mixed by means of a magnetic stirrer at about 25° C. (Mixture A1):

20.00 g of Additin® RC 5250
10.00 g of Pluriol® E 600
0.03 g of phosphoric acid, 75% by weight The acid number was 115.9 mg of KOH/g.

The Method for the Examples was as Follows:

5 drops were taken from the Mixture A1 and added to about 50 ml of drinking water of hardness 20° dH (sample A1) at about 25° C. After sample A1 had been mixed by stirring, insoluble droplets remained in the water.

20 g of the Mixture A1 were then heated in an open glass beaker at 120° C. with the use of a magnetic stirrer. After a reaction time of 6 hours, the reaction product, i.e. a mixture of the sulphur-bridged compounds of the invention, and where appropriate of unreacted starting materials and by-products, was cooled to room temperature (Mixture A2). 5 drops were likewise taken from the Mixture A2 and added to about 50 ml of drinking water of hardness 20° dH (sample A2). After the sample A2 had been mixed by stirring, the droplets were emulsified in water and formed an emulsion with coarse disperse phase.

Finally, a few drops of aqueous potassium hydroxide solution were added to each of the samples A1 and A2 until a pH>10 had been reached. In the neutralized sample A1, voluminous precipitate formed, and in the neutralized sample A2 an emulsion with fine disperse phase formed and exhibited a slight, fine sediment only after some days.

The table below collates the results of the Examples:

|  | Mixture A1 (Comparison) | Mixture A2 (Of the invention) |
| --- | --- | --- |
| Solubility in drinking water | Insoluble | Emulsion with coarse disperse phase |
| Solubility in drinking water after neutralization | Voluminous precipitate | Emulsion with fine disperse phase |
| Acid number measured after 6 hours | 115.9 mg of KOH/g | 85.4 mg of KOH/g |
| Corrected acid number (= measured acid number after deduction of the calculated acid number of the phosphoric acid content) | 114.6 mg of KOH/g | 84.1 mg of KOH/g |
| Measured sulphur content | 10.3% by weight | 10.3% by weight |

The Mixture A1 had reacted after a reaction time of 6 hours to give the product of the invention (Mixture A2). The sulphur-bridged compounds of the invention have 10.3% by weight sulphur content. The acid number of the product of the invention is 85.4 mg of KOH/g. The reduced acid number proves that within the sulphur-bridged compounds there are not only unesterified fatty acids but also polyethylene-glycol-esterified fatty acids (polyethylene glycol esters). The value for the Mixture A1 (Comparison) remained unchanged.

Quantitative studies were moreover carried out to determine soap scum deposit. To this end, each of the Mixtures A1 and A2 was dissolved at 0.3% by weight at about 25° C. in water according to DIN 51367 with a defined total hardness of 3.58 mmol/liter, corresponding to 20° dH. Aqueous potassium hydroxide solution (45% by weight) was admixed with each of these solutions until a pH of 11.0±0.2 had been achieved. In order to facilitate dissolution of the Mixtures A1 and A2 in water, most of the aqueous potassium hydroxide solution required was first dissolved in water. Each of the Mixtures A1 and A2 was then slowly added dropwise during constant stirring. Finally, a pH of 11.0±0.2 was established with the aqueous potassium hydroxide solution.

The 0.3 percent by weight solution of the Mixture A1 is termed Solution A1, and the 0.3 percent by weight solution of the Mixture A2 is termed Solution A2. The pH of the Solutions A1 and A2 was 11.0.

The freshly mixed Solution A1 comprised voluminous suspended precipitate; after 24 h the precipitate sunk to the bottom, and above the sediment there was an emulsion visible with fine disperse phase. The freshly mixed Solution A2 was an emulsion with fine disperse phase; after 24 h the emulsion still had a fine disperse phase, but a slight, fine sediment was apparent.

After 24 h, the matured Solutions A1 and A2 were filtered by using prepleated filters (Macherey-Nagel 615 ¼). The residues (soap scum) in the filter were dried at 105° C. for 2 b and analysed gravimetrically.

|  | Mixture A1 (Comparison) | Mixture A2 (Of the invention) |
| --- | --- | --- |
| Mass of residue (scum) | 0.89 g | 0.36 g |
| Input weight of mixture | 1.50 g | 1.50 g |
| Ratio of mass of residue to input weight of mixture | 59% by weight | 24% by weight |

In the case of the Mixture A1 the mass of the residue was 0.89 g. In the case of the Mixture A2 of the invention the mass of the residue was only 0.36 g.

SUMMARY

With the Inventive Examples it was possible to show clearly that when the product of the invention (Mixture A2) is used there was significantly less soap scum deposit.

Experiments have shown that the object of the present invention has been achieved. After adequate reaction time, the Mixture A1 was modified in such a way as to provide a product (Mixture A2) which is water-miscible without addition of emulsifier, and has high polarity, has no, or no significant, tendency towards formation of soap scum deposit in hard water, and has high sulphur content.

What is claimed is:

1. Sulphur-bridged compounds comprising at least one fatty acid bonded by way of at least one sulphur bridge to at least one polyalkylene glycol ester, wherein the polyalkylene glycol ester is the reaction product of at least one fatty acid with a polyalkylene glycol, and the sulphur-bridged compounds have 8 to 29% by weight sulphur content.

2. The sulphur-bridged compounds according to claim 1, wherein the polyalkylene glycol ester is polyethylene glycol ester, polypropylene glycol ester, polybutylene glycol ester and/or polyalkylene glycol esters in which the ethylene oxide units, propylene oxide units and/or butylene oxide units are in random and/or blockwise arrangement.

3. The sulphur-bridged compounds according to claim 1 or 2, wherein the sulphur-bridged compounds have the following formulae:

formula (I)
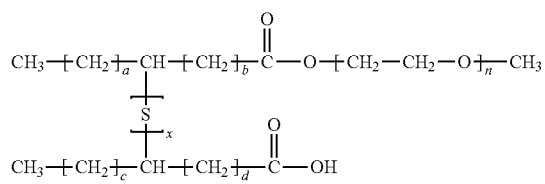
and/or
formula (II)
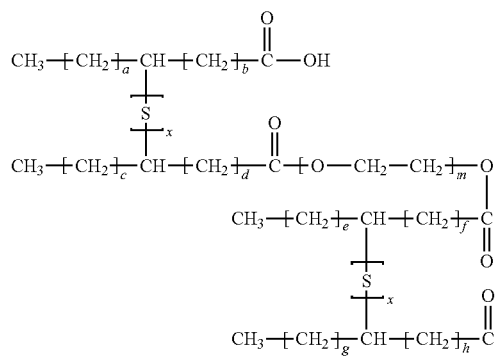
and/or
formula (III)
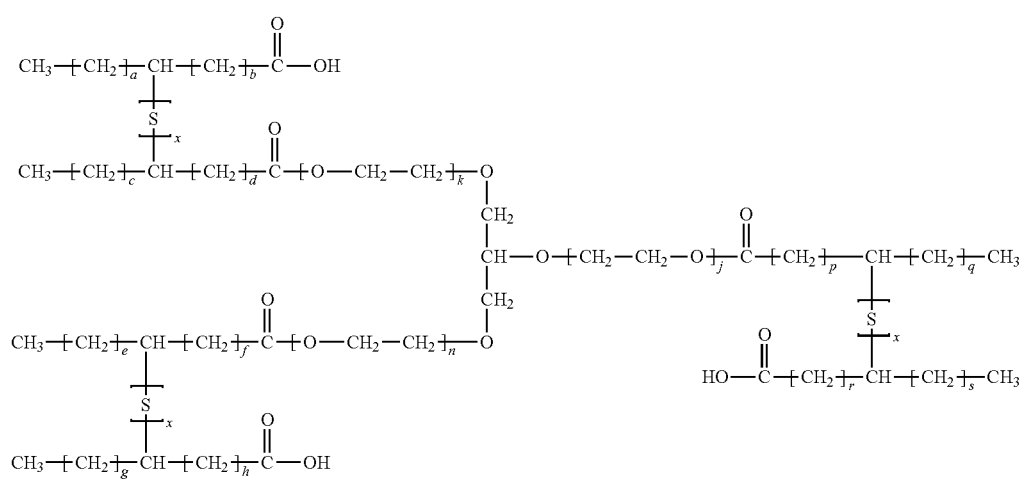
and/or
formula (IV)
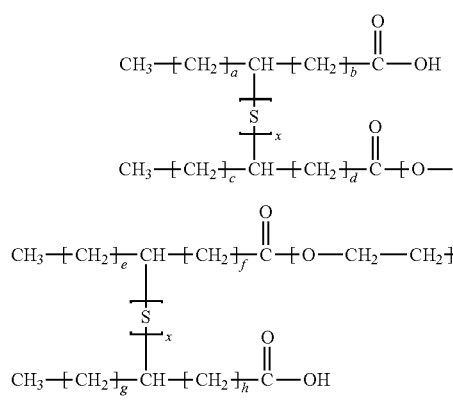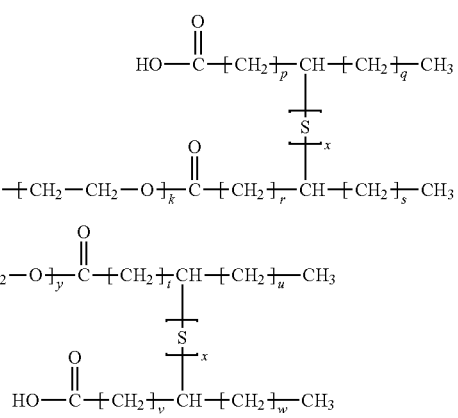

where a, b, c, d, e, f, g, h, p, q, r, s, t, u, v and w correspond mutually independently to values of 3 to 29, n, k, j and y correspond mutually independently to values of 2 to 10, m=4 to 20, and x=1 to 10.

4. A mixture comprising at least one sulphur-bridged compound according to claim 3, and at least one of lubricant additives and carrier liquids.

5. A process for the production of the sulphur-bridged compounds according to claim 1, the process comprising:

reacting the unsaturated fatty acid with sulphur and/or hydrogen sulphide to give the sulphur-bridged fatty acid, and reacting the sulphur-bridged fatty acid with the polyalkylene glycol in such a way that at least one carboxylic acid unit of the fatty acid is present within the sulphur-bridged compounds.

6. A process for the production of the sulphur-bridged compounds according to claim 1, the process comprising:

reacting a molar excess of unsaturated fatty acid with polyalkylene glycol to give an intermediate product composed of unsaturated polyalkylene glycol ester and unsaturated fatty acid, and reacting the intermediate product with sulphur and/or hydrogen sulphide in such a way that at least one carboxylic acid unit of the fatty acid is present within the sulphur-bridged compounds.

7. A process for the production of the sulphur-bridged compounds according to claim 1, the process comprising:

mixing the unsaturated fatty acid with at least one unsaturated fatty acid polyalkylene glycol ester, and reacting the mixture with sulphur and/or hydrogen sulphide in such a way that at least one carboxylic acid unit of the fatty acid is present within the sulphur-bridged compounds of the invention.

8. The process according to any of claims 5 to 7, wherein the unsaturated fatty acids are at least one of unsaturated monocarboxylic acids having a carbon-chain length of from 6 to 32 C atoms, and mixtures of unsaturated fatty acids.

9. The process according to any of claims 5 to 7, the sulphur is elemental sulphur.

10. The process according to any of claims 5 to 7, wherein the polyalkylene glycol comprises bifunctional polyethylene glycol.

11. The sulphur-bridged compounds according to claim 1, wherein the polyalkylene glycol ester is polyethylene glycol ester.

12. The sulphur-bridged compounds according to claim 3, wherein:

a, b, c, d, e, f, g, h, p, q, r, s, t, u, v and w correspond mutually independently to values of 5 to 12, n, k, j and y correspond mutually independently to values of 4 to 8, m=8 to 16, and x=2 to 4.

13. A mixture comprising at least one of sulphur-bridged compound according to claim 1 or 2, and at least one of lubricant additives and carrier liquids.

14. The sulphur-bridged compounds according to claim 1, wherein the sulphur-bridged compounds have greater than 10% to 29% by weight sulphur content.

15. Sulphur-bridged compounds comprising at least one fatty acid bonded to at least one polyalkylene glycol ester via at least one sulphur bridge, wherein the sulphur-bridged compounds have at least 8% by weight sulphur content.

16. The sulphur-bridged compounds according to claim 15, wherein:

the at least one fatty acid comprises unsaturated monocarboxylic acids having a carbon-chain length of from 6 to 32 C atoms; and the polyalkylene glycol ester is polyethylene glycol ester, polypropylene glycol ester, polybutylene glycol ester and/or polyalkylene glycol esters.

* * * * *